(12) United States Patent
Burnett et al.

(10) Patent No.: US 8,735,393 B2
(45) Date of Patent: *May 27, 2014

(54) ANHYDROUS TOPICAL SKIN PREPARATIONS

(75) Inventors: Katherine M. Burnett, Basking Ridge, NJ (US); Ellen S. Kurtz, Ringoes, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/560,761

(22) Filed: Jul. 27, 2012

(65) Prior Publication Data

US 2012/0321574 A1  Dec. 20, 2012

Related U.S. Application Data

(63) Continuation of application No. 10/722,134, filed on Nov. 26, 2003, now Pat. No. 8,232,276, which is a continuation of application No. 09/562,376, filed on May 1, 2000, now Pat. No. 7,179,475, which is a continuation-in-part of application No. 09/205,474, filed on Dec. 4, 1998, now Pat. No. 6,238,683.

(51) Int. Cl.
*A01N 43/58* (2006.01)
*A01N 43/60* (2006.01)
*A61K 31/50* (2006.01)
*A61K 31/495* (2006.01)
*A01N 43/26* (2006.01)
*A61K 31/415* (2006.01)
*A61K 31/355* (2006.01)
*A01N 25/34* (2006.01)

(52) U.S. Cl.
USPC ........... 514/250; 514/387; 514/463; 514/944; 424/404

(58) Field of Classification Search
USPC ................... 514/250, 387, 463, 944; 424/404
See application file for complete search history.

(56) References Cited

U.S. PATENT DOCUMENTS 5,208,257 A * 5/1993 Kabara .......................... 514/552
5,993,787 A * 11/1999 Sun et al. ......................... 424/59

* cited by examiner

*Primary Examiner* — Kendra D Carter
(74) *Attorney, Agent, or Firm* — Leydig, Voit & Mayer, Ltd.

(57) ABSTRACT

The present invention provides anhydrous compositions for topical delivery of a medicament comprising (A) a penetration enhancer/solvent selected from the group consisting of alcohol, propylene glycol, or a combination thereof; (B) a humectant/solvent selected from the group consisting of polyethylene glycol, glycerin, sorbitol, xylitol, or any combination of any of the foregoing; and (C) an anhydrous vehicle. In an alternate embodiment, the present invention provides anhydrous compositions for topical delivery of a medicament which comprise (A) a penetration enhancer/solvent selected from the group consisting of alcohol, propylene glycol, or a combination thereof; (B) a humectant/solvent selected from the group consisting of polyethylene glycol, glycerin, sorbitol, xylitol or any combination of any of the foregoing; (C) an anhydrous vehicle; and (D) a medicament. Also provided are methods for topically delivering a medicament to an animal.

6 Claims, No Drawings

ANHYDROUS TOPICAL SKIN PREPARATIONS

CROSS-REFERENCE TO RELATED APPLICATIONS

This patent application is a continuation of U.S. patent application Ser. No. 10/722,134, filed Nov. 26, 2003, now U.S. Pat. No. 8,232,276, which is a continuation of U.S. patent application Ser. No. 09/562,376 filed May 1, 2000, now U.S. Pat. No. 7,179,475, which is a continuation-in-part of U.S. patent application Ser. No. 09/205,474 filed Dec. 4, 1998, now U.S. Pat. No. 6,238,683, the disclosures of which is incorporated herein by reference in their entireties.

FIELD OF THE INVENTION

The present invention relates to topical anhydrous skin preparations having high therapeutic efficacy, low toxicity, and the ability to target or enhance delivery of active agents to the skin, thereby resulting in an improved, high therapeutic index. The invention further relates to methods for making and using such compositions.

BACKGROUND OF THE INVENTION

Alcohols, polyols (such as, for example, propylene glycol), surfactants (such as, for example, sodium lauryl sulfate), preservatives (such as, for example, parabens, such as methyl paraben), acids (such as, for example, sorbic acid), and solvents, singly or in topical preparations, are known either to induce irritation, sensitization, or allergic skin reactions and/ or to be skin penetration enhancers. Humectants (such as for example, glycerin), solvents (such as, for example, polyethylene glycol), sunscreens (such as, for example, zinc oxide), and surfactants are among the entities known to retard skin penetration of active agents. See, Angleini, G. *Contact Dermatitis* 7, 1981; Belmonte, J. *Pharm Sci* 67: 517, 1978; Catanzaro, J. M. *J Am Acad Dermatol* 24 (1), 1981; Cooper, *J Pharm Sci* 73: 1153, 1984; Faucher, *J Am Oil Chem Soc* 56: 776, 1979; Lahti, A. *Contact Dermatitis* 29, 1993; Trancik, R. J., *Contact Dermatitis* 8, 1982; Wahlberg, J. E. *Acta Derm Venereol* 64, 1984; Zatz, J. L. *J Soc Cosmet Chem* 34: 327, 1983.

Patel et al., U.S. Pat. No. 4,855,294, disclose a composition containing glycerin and a method for reducing skin irritation properties of a transdermal (i.e., delivery by actual passage of a drug through the skin or mucosal tissue) drug enhancer composition.

Glucocorticosteroid-based compositions have been used since the 1940's to treat inflammations of the skin. World Patent Publication No. WO92/18113 discloses a liquid solution containing an antifungal agent and a steroid for use as a mouthwash. Hogi, F. *Mykosen* 23(8): 426, 1980 reports on the activity of ketoconazole in the presence of triaminolene acetonide. Ketoconazole compositions have more recently been proved to be effective in the treatment of mycotic infections.

Skin diseases are often characterized by the combination of both inflammatory conditions and fungal infections, since inflammatory processes of the skin create predisposing conditions for the growth and proliferation of pathogenic microorganisms. Therefore, a single drug-therapy with an antiinflammatory or an antifungal agent alone is often insufficient to treat various skin diseases.

U.S. Pat. No. 5,654,293 and EP Patent Publication No. 0 680 328 describe a topical oil in water emulsion and pharmaceutical composition respectively comprising ketoconazole and an acetonide glucocorticosteroid having a pH above 2.5 and below 6.

However, the stability problems involved combining a 17-ester steroid with an imidazole antifungal agent are known from U.S. Pat. Nos. 5,002,938 and 5,110,809. The preparation of a formulation containing both ketoconazole and a glucocorticosteroid was hindered by the destabilization of the steroid in the presence of ketoconazole. There continues to be an unmet clinical need for topically stable, efficacious, and nontoxic therapies targeted to the skin for the treatment of skin disorders. Therefore, applications of and the opportunity for new methods for making these compositions are needed.

SUMMARY OF THE INVENTION

According to an embodiment of the present invention, there are provided anhydrous compositions for topical delivery of one or more medicaments. These compositions comprise:

(A) a penetration enhancer/solvent selected from the group consisting of alcohol, propylene glycol, or a combination thereof;

(B) a humectant/solvent selected from the group consisting of polyethylene glycol, glycerin, sorbitol, xylitol, or any combination of any of the foregoing; and (C) an anhydrous vehicle.

According to an alternate embodiment of the present invention, there are provided anhydrous compositions for topical delivery of one or more medicaments which comprise:

(A) a penetration enhancer/solvent selected from the group consisting of alcohol, propylene glycol, or a combination thereof;

(B) a humectant/solvent selected from the group consisting of polyethylene glycol, glycerin, sorbitol, xylitol or any combination of any of the foregoing;

(C) an anhydrous vehicle; and (D) one or more medicaments.

According to another embodiment of the present invention, there are provided methods for topically delivering one or more medicaments to an animal, such as a mammal or a human patient, in need of the medicaments. The methods comprise topically administering to the animal compositions as described above.

DETAILED DESCRIPTION OF THE INVENTION

The compositions of the present invention typically are creams, gels, ointments, lotions or liquids. These compositions are anhydrous in that no water is added. However, a certain amount of water associated with the various components may be contained in the composition. Typically, this will be less than 10 percent by weight, based upon 100 percent by weight of total composition. Preferably, the present compositions are completely anhydrous.

Penetration enhancers/solvents suitable for use in the present invention are alcohols, including, but not limited to, ethanol, propylene glycol, or a combination thereof. Suitable humectants/solvents for use herein, include, but are not limited to, polyethylene glycol, glycerin, sorbitol, xylitol or any combination of any of the foregoing. Suitable anhydrous vehicles for use herein include, but are not limited to, alcohols which may be the same as or different than the alcohol penetration enhancer. Non-limiting examples of such alcohols are isobutanol and isopropyl alcohol.

Medicaments which may be delivered topically in the present compositions include, but are not limited to, antifungal agents, antibacterial agents, antiviral agents, antiacne agents, antiaging agents, antipruritic agents, photoprotection agents, skin pigment modulators, hair growth enhancers, hair growth inhibitors, hair removal agents, antidandruff agents, anti-seborrheic agents, anti-psoriasis agents, exfoliating agents, wound healing agents, anti-ectoparasitic agents, sebum modulators, immunomodulators, hormones, botanicals, moisturizers, astringents, cleansers, sensates, antibiotics, anti-irritants, anesthetics, analgesics, steroids, anti-inflammatories, tissue healing substances, tissue regenerating substances, vitamins including, but not limited to, retinoids and the like, amino acids, peptides, minerals, hydroxy acids, including, but not limited to, alpha hydroxy acids and beta hydroxy acids, or any combination of any of the foregoing.

Non-limiting examples of steroids are glucocorticosteroids and particularly desonide. A non-limiting example of an antibiotic is erythromycin. Azole-type antifungal and antibacterial agents, such as imidazole antifungal and antibacterial agents, may be employed in the compositions of this invention in their base form. For example, ketoconazole, miconazole, itraconazole, metronidazole, elubiol, and like related imidazole antifungals and antibacterials known to those of skill in the art are useful in the topical formulations of this invention. A preferred antifungal agent is ketoconazole.

Other components which may be contained in the compositions of the present invention include, but are not limited to, emollients, chelating agents, pH adjusters, antioxidants, gelling agents, viscosifiers, colorants, fragrances, UV stabilizers, sunscreens, or any combination of any of the foregoing.

Non-limiting examples of pH adjusters are malic acid, lactic acid, citric acid, glycolic acid, benzoic acid, ascorbic acid, or any combination of any of the foregoing. Non-limiting examples of antioxidants are propyl gallate, ascorbic acid, ascorbyl palmitate, butylated hydroxyanisole (BHA), butylated hydroxytoluene (BHT), tocopherol, such as alpha-tocopherol, or any combination of any of the foregoing. A non-limiting example of a viscosifier is hydroxypropyl cellulose.

The amounts of each of the components of the present composition are typically those amounts effective to accomplish the purpose of that ingredient. For example, the amount of penetration enhancer is typically a penetration enhancing effective amount. Preferably, the compositions include from about 1.0 to about 50 percent by weight of penetration enhancer/solvent, from about 10 to about 80 percent by weight of humectant/solvent, from 0 to about 10 percent by weight of emollient and aesthetic enhancer combined, from 0 to about 2 percent by weight of chelating agent and pH adjuster combined, from 0 to about 2 percent by weight of antioxidant, from 0 to about 5 percent by weight of gelling agent and viscosifier combined, and an anhydrous vehicle, based upon 100 percent by weight of total composition.

Preferably, the amount of hydroxypropyl cellulose gelling agent will range from 0 to about 3 percent by weight, based upon 100 percent by weight of total composition.

Preferred amounts of specific medicaments are from about 0.0001 to about 20 percent by weight, preferably from about 0.5 to about 3 percent by weight, and most preferably about 2 percent by weight of an antifungal agent and particularly ketoconazole; from about 0.0001 to about 10 percent by weight, preferably from about 0.01 percent to about 2.0 percent by weight, and most preferably about 0.05 percent by weight, of a glucocorticosteroid and particularly desonide; preferably from about 0.001 to about 0.5 percent by weight, and most preferably from about 0.02 to about 0.1 percent by weight of a vitamin and particularly an all-trans retinoic acid, tretonoin; and preferably from about 0.01 to about 10 percent by weight, and most preferably from about 0.1 to about 3 percent by weight of an antibiotic and particularly erythromycin, based upon 100 percent by weight of total composition.

The amount of the penetration enhancer, solvent and vehicle may be balanced to solubilize the medicament.

The compositions of the present invention are administered topically in therapeutically effective amounts of the medicament incorporated therein. The compositions of the present invention may be prepared by mixing the penetration enhancer/solvent, humectant/solvent, and anhydrous vehicle in a primary vessel until uniform. Medicaments or active agents can then be added and mixed until uniform. Any chelating agents, pH adjusters, antioxidants, emollients, aesthetic enhancers, fragrances, UV stabilizers, sunscreens, colorants and the like can then be added and mixed until uniform. Viscosifiers and gelling agents may then be added and mixed until uniform. The final product may then be packaged.

DESCRIPTION OF THE PREFERRED EMBODIMENTS

The following examples illustrate the invention without limitation. All amounts are given by percent by weight based upon 100 percent by weight of total composition, unless noted otherwise.

Example 1

An anhydrous composition for topical administration of ketoconazole and desonide was prepared having the formulation of Table 1 below.

TABLE 1

Ketoconazole/Desonide Formulation

| Ingredient | % w/w |
|---|---|
| ketoconazole | 0-2 |
| desonide | 0.0-0.05 |
| propylene glycol | 20 |
| polyethylene glycol | 20 |
| glycerin | 20 |
| PPG-15 stearyl ether | 0-2 |
| hydroxypropyl cellulose | 1.5-2.0 |
| ascorbic acid | 0.0-0.3 |
| citric acid | 0.0-0.1 |
| butylated hydroxytoluene | 0.0-0.1 |
| Ethanol q.s. to | 100 |

Comparative Examples 1A-C

Compositions having the formulations of Tables 2-4 below were prepared.

TABLE 2

Ketoconazole/Desonide Formulation

| Ingredient | % w/w |
|---|---|
| ketoconazole | 0-2 |
| desonide | 0.0-0.05 |
| propylene glycol | 10 |
| stearyl alcohol | 4 |
| cetyl alcohol | 4 |
| sorbitan monostearate | 2 |
| polysorbate 60 | 1.5 |
| mineral oil | 1 |

TABLE 2-continued

Ketoconazole/Desonide Formulation

| Ingredient | % w/w |
|---|---|
| dibasic sodium phosphate | 0.25 |
| citric acid | 0.24 |
| benzoic acid | 0.2 |
| butylated hydroxyanisole | 0.005 |
| purified water | 100 |

TABLE 3

Ketoconazole/Desonide Formulation

| Ingredient | % w/w |
|---|---|
| ketoconazole | 0-2 |
| desonide | 0.0-0.05 |
| propylene glycol | 20 |
| polyethylene glycol | 10 |
| glycerin | 30 |
| PPG-15 stearyl ether | 2 |
| hydroxylpropyl cellulose | 1.5-2.0 |
| ascorbic acid | 0-0.3 |
| citric acid | 0-0.1 |
| butylated hydroxytoluene | 0-0.1 |
| Ethanol q.s. to | 100 |

TABLE 4

Ketoconazole/Desonide Formulation

| Ingredient | % w/w |
|---|---|
| ketoconazole | 0-2 |
| desonide | 0.0-0.05 |
| propylene glycol | 20 |
| N-methyl-2-pyrrolidone | 20 |
| glycerin | 20 |
| PPG-15 stearyl ether | 2 |
| hydroxylpropyl cellulose | 1.5-2.0 |
| ascorbic acid | 0.0-0.3 |
| citric acid | 0.0-0.1 |
| butylated hydroxytoluene | 0.0-0.1 |
| Ethanol q.s. to | 100 |

Example 2

An anhydrous composition for topical administration of all-trans retinoic acid as known as tretinoin, was prepared having the formulation of Table 5 below.

TABLE 5

Tretinoin Formulation

| Ingredient | % w/w |
|---|---|
| tretinoin | 0.05 |
| propylene glycol | 20 |
| polyethylene glycol | 20 |
| glycerin | 20 |
| PPG-15 stearyl ether | 0-2 |
| hydroxylpropyl cellulose | 1.5-2.0 |
| citric acid | 0.0-0.15 |
| butylated hydroxytoluene | −0.1 |
| Ethanol q.s. to | 100 |

Example 3

An anhydrous composition for topical administration of erythromycin was prepared having the formulation of Table 6 below.

TABLE 6

Erythromycin Formulation

| Ingredient | % w/w |
|---|---|
| Erythromycin | 2 |
| propylene glycol | 20 |
| polyethylene glycol | 20 |
| glycerin | 20 |
| PPG-15 stearyl ether | 0-2 |
| hydroxylpropyl cellulose | 1.5-2.0 |
| citric acid | 0.0-0.5 |
| Ethanol q.s. to | 100 |

Example 4 and Comparative Example 4A

Skin Inflammation Assay

Topically applied phorbol esters are known inducers of skin inflammation. Corticosteroids are known to be highly effective in lowering phorbol ester (e.g. TPA) induced inflammation in a dose dependent fashion. Therefore, this model was used to evaluate the relative anti-inflammatory activity of corticosteroids.

Dose response studies to reduce skin inflammation (TPA ear edema in a murine model) were conducted with the compositions of Example 1 (Example 4) and Comparative Example 1A (Comparative Example 4A). Results are illustrated in Table 7 below.

TABLE 7

Skin Anti-Inflammatory Activity

| | Example 4 | | Comparative Example 4 | |
|---|---|---|---|---|
| % Desonide | % Inhibition | $ED_{50}$ (%) | % Inhibition | $ED_{50}$ (%) |
| 0.0000 | 0 | 0.0015 | 0 | 0.0054 |
| 0.0003 | 30.40 | | 15.36 | |
| 0.003 | 57.43 | | 39.05 | |
| 0.03 | 87.08 | | 74.79 | |

The composition of Example 1 (Example 4) ($ED_{50}$=0.0015%) was topically three times more active and more potent in its skin anti-inflammatory activity than that of Comparative Example 1A (Comparative Example 4A) ($ED_{50}$=0.0054%).

Example 5 and Comparative Examples 5A and 5B

Skin Antifungal Assay

Microbiological in vitro cadaver skin zone of inhibition studies were conducted to measure antifungal activity and to demonstrate biological activity on the human skin using the compounds of Example 1 (Example 5), Comparative Example 1A (Comparative Example 5A), and NIZORAL® cream (2% ketoconazole cream) (Janssen Pharmaceutica) (Comparative Example 5B). Results are illustrated in Table 8 below.

TABLE 8

Skin Antifungal Activity

|  | Clear Zone for P. ovale | Clear Zone for T. rubrum |
|---|---|---|
| Example 5 | 11 mm | 13 mm |
| Comparative Example 5A | 3 mm | 0[1] |
| Comparative Example 5B | 3 | 0[1] |

[1]Only a partial zone of inhibition was noted for this organism where it continued to grow; no clear zone resulted.

*T. rubrum* is a major organism known to cause skin fungal disorders including tinea corporis, tinea cruris, and tinea pedis. Results indicated that the composition of Example 1 (Example 5) demonstrated significant skin antifungal (clear zone) activity against the common dermatophyte *T. rubrum*. The composition of Comparative Example 1A (Comparative Example 5A) and NIZORAL® cream (Comparative Example 5B) did not demonstrate clear zone antifungal activity for *T. rubrum* in this study.

*P. ovale* has been implicated as playing a major role in the etiology of various dermatoses, such as Seborrheic Dermatitis. The composition of Example 1 (Example 5) also demonstrated outstanding antifungal activity against the yeast, *P. ovale*, while that of Comparative Example 1A (Comparative Example 5A) and NIZORAL® cream (Comparative Example 5B) only showed minimal activity.

Examples 6 and 7 and Comparative Examples 6A-E and 7A

Measurement of Targeted and Enhanced Delivery to Skin

Franz cell diffusion studies using human cadaver skin were conducted to demonstrate cutaneous bioavailability of medicaments like ketoconazole and desonide using the compositions of Example 1 (Examples 6 and 7), NIZORAL® cream (Comparative Examples 6A, 6C, and 6E), DesOwen® cream (0.05% desonide cream) (Galderma) (Comparative Examples 7B, 7C, and 7E), Example 1A (Comparative Examples 6B and 7A), and Comparative Example 1B (Comparative Examples 6D and 7F).

Results are illustrated in Tables 9 and 10 below.

TABLE 9

Ketoconazole Targeted Delivery to the Skin

|  | Formulation | Epidermis | Dermis | Receptor |
|---|---|---|---|---|
| Example |  |  |  |  |
| 6B | 2% ketoconazole, 0.05% (desonide) | 0.33 ± 0 | 0.55 ± 0 | 0.2 ± 0 |
| 6C | (2% ketoconazole cream) | 0.64 ± 0.0 | 1.18 ± 0.0 | 0.12 ± 0.0 |
| Test 2 |  |  |  |  |
| 6 | (2% ketoconazole, 0.05% desonide) | 2.44 ± 0.65 | 1.24 ± 0.78 | 0.5 ± 0.05 |
| 6A | (2% ketoconazole cream) | 0.205 ± 0.01 | 0.371 ± 0.10 | 1.017 ± 0.24 |
| Test 3 |  |  |  |  |
| 6D | (2% ketoconazole, 0.05% desonide) | 1.83 ± 0.37 | 1.77 ± 1.01 | 0.950 ± 0.43 |

TABLE 9-continued

Ketoconazole Targeted Delivery to the Skin

|  | Formulation | Epidermis | Dermis | Receptor |
|---|---|---|---|---|
| 6E | (2% ketoconazole cream) | 0.112 ± 0.03 | 0.195 ± 0.08 | 0.428 ± 0.15 |

TABLE 10

Desonide Targeted Delivery to the Skin

|  | Formulation | Epidermis | Dermis | Receptor |
|---|---|---|---|---|
| Example |  |  |  |  |
| 7A | 2% ketoconazole, 0.05% (desonide) | 2.64 ± 0 | 1.85 ± 0 | 1.6 ± 0 |
| 7B | (0.05% desonide cream) | 2.57 ± 0 | 2.03 ± 0 | 2.99 ± 0 |
| Test 2 |  |  |  |  |
| 7 | (2% ketoconazole, 0.05% desonide) | 1.222 ± 1.35 | 1.125 ± 0.88 | 0.677 ± 0.06 |
| 7C | (0.05% desonide cream) | 1.372 ± 0.21 | 0.718 ± 0.43 | 12.49 ± 1.83 |
| Test 3 |  |  |  |  |
| 7D | (2% ketoconazole, 0.05% desonide) | 1.359 ± 0.44 | 1.905 ± 1.09 | 0.516 ± 0.1 |
| 7E | (2% desonide cream) | 0.853 ± 0.03 | 1.104 ± 0.31 | 3.677 ± 1.24 |

The composition of Example 1 demonstrated targeted delivery of ketoconazole and desonide to the cutaneous compartments. It delivered greater amount of ketoconazole to the epidermis and dermis but less to the receptor versus NIZORAL® cream. A comparable amount of desonide from the composition of Example 1 was delivered to the epidermis and to the dermis and less to the receptor versus DesOwen® cream (Comparative Examples 7B, 7C, and 7E). Diminished amounts of ketoconazole and desonide medicaments in the receptor compartment of the composition of Example 1 may clinically translate to lower systemic absorption of the drugs and, thereby, lower systemic drug toxicity. The composition of Comparison Example 1A versus NIZORAL® and DesOwen® creams delivered less ketoconazole to the epidermis and dermis but a greater amount to the receptor versus NIZORAL® cream.

Overall results indicate that the composition of Example 1 resulted in targeted delivery of the drugs to the skin with greater amounts of medicaments to the intended sites of the epidermis and dermis versus that of Comparative Example 1A, NIZORAL® cream and DesOwen® cream. The data demonstrates better targeted delivery to the skin and more pharmacologic effects due to the composition of Example 1. Moreover, the composition of Example 1 demonstrated positively less permeation through the skin into the receptor that could clinically translate into lower systemic toxicity. In contrast, the composition of Comparative Example 1A results indicate greater permeation of ketoconazole into the receptor fluid that could exhibit negative clinical, toxic systemic effects.

Example 8 and Comparative Examples 8A and 8B

Cumulative Irritation Test

Dermal irritation studies of the compositions of Example 1 (Example 8), Comparative Example 1B (Comparative Example 8A), and Comparative Example 1C (Comparative Example 8B) were conducted on albino rabbits to determine relative irritation using mean grades of erythema and edema. Results are illustrated in Table 11.

As shown in Table 11, the composition of Example 1 was less irritating than that of Comparative Examples 1B and 1C ($p<0.05$). Glycerin alone did not singly reduce irritations.

In addition, the combination of the diminished irritation the composition of Example 1 and its enhanced efficacy translated into an improved, high Therapeutic Index.

TABLE 11

Cumulative Irritation Test (Combined Daily Erythema and Edema Score)

| | Day | | | | |
|---|---|---|---|---|---|
| | 0 | 5 | 10 | 15 | 19 |
| Example 8 | 0 | 1.6 | 2.6 | 1.8 | 0.7 |
| Comparative Example 8A | 0 | 2.4 | 3.5 | 3.1 | 1.3 |
| Comparative Example 8B | 0 | 2.5 | 3.9 | 3.1 | 1.5 |

Example 9

Repeated Patch Insult Test

The vehicle composition of Example 1, i.e., the composition without ketaconazole or desonide, was evaluated for the potential to induce contact dermal sensitization in human subjects.

A total of 216 male and female subjects were evaluated over a period of six weeks. After selection, a semi-occlusive patch with test material was applied nine times over three weeks. Following a rest period and test site observation, a challenge test was conducted.

During the induction phase, three subjects exhibited low-level reactions. Two other subjects exhibited dryness only. Original test sites exhibited no reactions on subjects during the rest period and at the challenge. Only two subjects exhibited low-level reactions at the challenge phase.

These clinical results indicate that the vehicle composition of Example 1, after repeated application, did not induce contact dermal sensitization in human subjects.

All patents, publications, applications, and test methods mentioned herein are hereby incorporated by reference.

Many variations of the present invention will suggest themselves to those skilled in the art in light of the above, detailed description. All such obvious variations are within the full intended scope of the appended claims.

The invention claimed is:

1. An anhydrous composition formulated for topical delivery consisting of:
   (a) about 20 percent by weight of propylene glycol,
   (b) about 20 percent by weight of polyethylene glycol,
   (c) about 20 percent by weight of glycerin,
   (d) about 34 percent by weight of ethanol,
   (e) about 2 percent by weight of ketoconazole,
   (f) PPG-15 stearyl ether,
   (g) hydroxypropyl cellulose,
   (h) ascorbic acid,
   (i) butylated hydroxytoluene,
   (j) citric acid, and
   (k) at least one colorant,
   wherein the composition is formulated as an anhydrous gel.

2. The composition of claim 1 wherein the ketoconazole is solubilized.

3. An anhydrous composition formulated for topical delivery consisting of:
   (a) about 20 percent by weight of propylene glycol,
   (b) about 20 percent by weight of polyethylene glycol,
   (c) about 20 percent by weight of glycerin,
   (d) about 34 percent by weight of ethanol,
   (e) about 2 percent by weight ketoconazole,
   (f) PPG-15 stearyl ether,
   (g) hydroxypropyl cellulose,
   (h) ascorbic acid,
   (i) butylated hydroxytoluene,
   (j) citric acid, and
   (k) at least one member selected from the group consisting of a colorant, fragrance, UV stabilizer and sunscreen,
   wherein the composition is formulated as an anhydrous gel.

4. An anhydrous composition formulated for topical delivery consisting of:
   (a) about 20 percent by weight of propylene glycol,
   (b) about 20 percent by weight of polyethylene glycol,
   (c) about 20 percent by weight of glycerin,
   (d) about 34 percent by weight of ethanol,
   (e) about 2 percent by weight ketoconazole,
   (f) PPG-15 stearyl ether,
   (g) hydroxypropyl cellulose,
   (h) ascorbic acid,
   (i) butylated hydroxytoluene, and
   (j) citric acid,
   wherein the composition is formulated as an anhydrous gel.

5. The composition of claim 3 wherein the ketoconazole is solubilized.

6. The composition of claim 4 wherein the ketoconazole is solubilized.

* * * * *